United States Patent
Adachi et al.

(10) Patent No.: US 7,095,024 B2
(45) Date of Patent: Aug. 22, 2006

(54) TEM SAMPLE EQUIPPED WITH AN IDENTIFYING FUNCTION, FOCUSED ION BEAM DEVICE FOR PROCESSING TEM SAMPLE, AND TRANSMISSION ELECTRON MICROSCOPE

(75) Inventors: Tatsuya Adachi, Chiba (JP); Toshiaki Fujii, Chiba (JP); Masashi Iwatsuki, Tokyo (JP); Mikio Naruse, Tokyo (JP); Mike Hassel Shearer, Peabody, MA (US)

(73) Assignees: SII NanoTechnology Inc., Chiba (JP); JEOL Ltd., Akishima (JP)

( * ) Notice: Subject to any disclaimer, the term of this patent is extended or adjusted under 35 U.S.C. 154(b) by 0 days.

(21) Appl. No.: 10/828,001

(22) Filed: Apr. 20, 2004

(65) Prior Publication Data

US 2004/0227082 A1    Nov. 18, 2004

(30) Foreign Application Priority Data

Apr. 22, 2003   (JP)   ............... 2003-117396

(51) Int. Cl.
*H01J 37/26* (2006.01)
*H01J 37/304* (2006.01)

(52) U.S. Cl. ............... 250/311; 250/492.21; 250/310; 250/309

(58) Field of Classification Search ............... 250/311, 250/307

See application file for complete search history.

(56) References Cited

U.S. PATENT DOCUMENTS 5,783,830 A * 7/1998 Hirose et al. .......... 250/492.21
6,576,900 B1 * 6/2003 Kelly et al. ................. 250/307
2003/0236586 A1* 12/2003 Tomimatsu et al. ......... 700/110

FOREIGN PATENT DOCUMENTS

JP          04282545 A   * 10/1992

* cited by examiner

*Primary Examiner*—Jack I. Berman
(74) *Attorney, Agent, or Firm*—Adams & Wilks

(57) ABSTRACT

The problem of the present invention is to provide a TEM sample equipped with an identifying function for easily specifying a detailed TEM sample and to provide a system for handling the management of information relating to the TEM sample using the TEM when making observations that is constructed with the FIB device manufacturing the sample. The TEM sample of the present invention is written with a mark encoding information specifying the sample at a specified location of a peripheral part. Information relating to the sample filed taking sample specifying information as an index is supplied to a TEM as associated matter. The sample working FIB device and observation TEM device of the present invention are provided with a function enabling writing of information relating to the sample and images to the file during operation which is then read out and utilized on a display.

9 Claims, 4 Drawing Sheets

TEM SAMPLE, DEPOSITION LAYER, REAR HOLE, MARK, FRONT HOLE, BOTTOM CUTTING, SIDE CUTTING

TEM SAMPLE

STORAGE MEDIUM [SAMPLE DATA FILE]

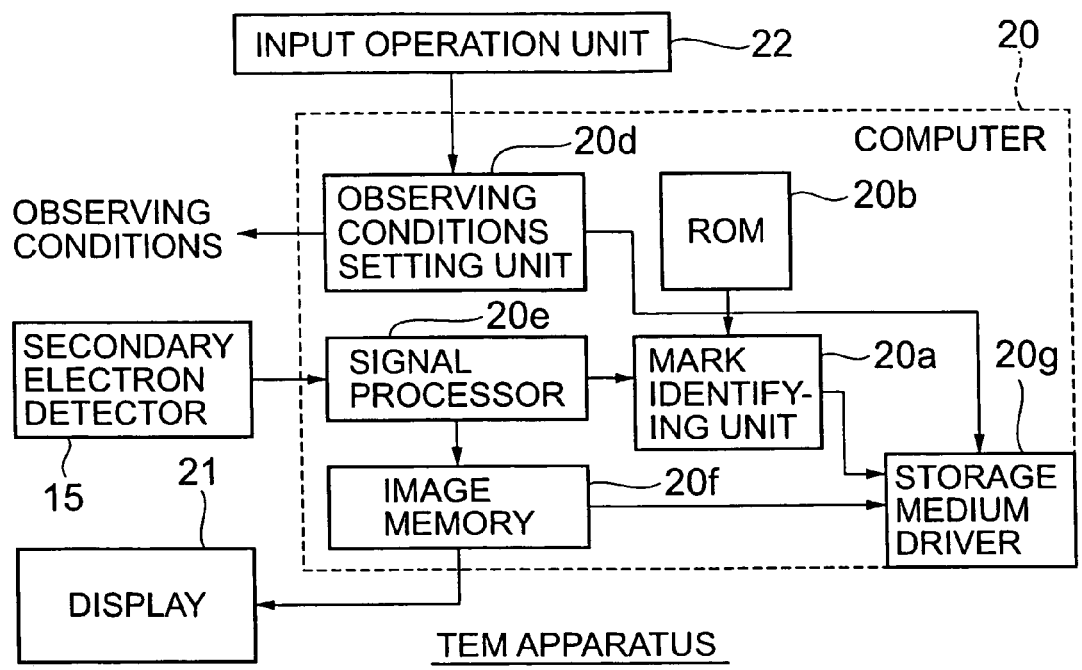

TEM SAMPLE EQUIPPED WITH AN IDENTIFYING FUNCTION, FOCUSED ION BEAM DEVICE FOR PROCESSING TEM SAMPLE, AND TRANSMISSION ELECTRON MICROSCOPE

BACKGROUND OF THE INVENTION

1. Field of the Invention

The present invention relates to a transmission electron microscope (hereinafter referred to as TEM) sample marked with self-identifying information in a coded manner, and a TEM sample management system constructed between a focused ion beam (hereinafter referred to as FIB) device for producing the sample and a TEM for observing the sample.

2. Description of the Related Art

Making of semiconductor sliced samples for TEM observation by thin-processing using an FIB device is well-known. A method where a small part is cut-out mechanically from a wafer-shaped sample and this is processed to be thin and a method where etching processing is carried out on a wafer as is so as to extract a thin sample are well-known. The present invention relates to TEM samples made using the latter method. This TEM sample manufacturing method is as follows. First, a protective deposition film is formed by irradiating a processing portion shown in FIG. 4A with an ion beam while ejecting source gas using a gas gun. As shown in FIG. 4B, a trench is then dug by irradiating a FIB from above the surface of the sample by etching processing at the rear side of an observation slice, and in a similar method shown in FIG. 4C, digging out takes place using etching processing at a front side of the observation slice. Namely, a square front hole and rear hole are made on either side of thin slice for observation using an FIB device. The size of the front hole is of a size capable of enabling observation of the observation slice at the time of tilting the sample table with a Scanning Ion Microscope (hereinafter referred to as a "SIM"), with the rear hole being of such a size that the width is the same as the front hole but the depth is in the order of two thirds that of the front hole. As the observation surface is damaged by the digging processing, finishing processing is carried out while suppressing beam current and the surface is polished. Next, the sample surface is tilted, and peripheral parts of the sample thin-processed as an observation slice as shown in FIG. 4D are irradiated with a focused ion beam as shown by the arrow so as to carry out cutting processing (bottom cutting). Then, as shown in FIG. 5A–5D, a manipulator (glass probe) is operated (FIG. 5A), this cut sample(sample chip) is separated from the sample body (FIG. 5B), and is moved so as to be positioned on a mesh (150 mesh) provided with a collodion film (FIG. 5C). The cut sample is then attached onto the mesh surface (FIG. 5D), and making of the sample for TEM observation is completed. The completed sample is what the cut sample with sides in the order of 10 μm is fixed to a mesh base of diameter of approximately 3 mm, and this handling management is troublesome due to the sample being extremely small in size.

There has therefore been a demand for development of a more reasonable management means for handling TEM samples that are extremely small in size under these kinds of conditions. A convenient method for accessing locations to be observed in detail on the microscope sample is disclosed in Japanese Patent Laid-open Publication No. Hei. 4-282545 (page three, sections three and four, FIG. 1). This method employs an FIB device so that, while an SEM or TEM sample is being subjected to processing, noted observation regions such as defects, etc. present on the same sample can be easily accessed even when a plurality of such regions exist. As shown in FIG. 6, symbols referred to as characters that make the noted observation regions distinctive are processed using an FIB in the vicinity of the area processed using the FIB. Even when it is said that the TEM sample is handled, after implementing thin-processing, this technological theory is based on the problem of, rather than the TEM sample cut-away fixed to the mesh, making specifying the position easier during accessing of the observation slice on a large sample such as a wafer, etc. for processing in a prior processing stage, and as such does not resolve the problem of the difficulty of managing the handling of the TEM sample itself due to the sample being of an extremely small size.

The object of the present invention is to provide a TEM sample equipped with an identifying function for easily specifying a detailed TEM sample and to provide a system for easily managing and handling information relating to the TEM sample using the TEM when making observations that is constructed with the FIB device manufacturing the sample.

SUMMARY OF THE INVENTION

A TEM sample of the present invention is written with a mark at a specific location of a peripheral part of the thin-processed TEM sample encoded with information specifying the sample and/or information associated with the sample. The sample is provided to a TEM apparatus along with a storage medium having information related to thin-processing of the TEM sample, the information being filed in the storage medium taking the sample-specifying information as an index.

The focused ion beam device for TEM sample processing of the system of the present invention is comprised of a function for writing marks encoding a TEM sample-specifying information onto the surface of the TEM sample and a function for filing an information related to the written TEM sample in a storage medium taking the sample-specifying information as an index. The FIB device for TEM sample processing of the system of the present invention is also comprised of a function for reading the mark encoded with the sample-specifying information and recognizing the specific information and a function for reading information relating to the sample taking the specific information as an index from the storage medium and displaying this on the display. A further function is also provided for rewriting TEM sample relationship information acquired by observation with an information file relating to the sample filed taking the sample-specifying information as an index and put in the form of a database together with other sample information.

BRIEF DESCRIPTION OF THE DRAWINGS

FIG. 2 is a block view illustrating the main functions of the FIB device for TEM sample processing according to the present invention.

FIGS. 4A–4B are views illustrating the TEM sample working process.

DETAILED DESCRIPTION OF THE PREFERRED EMBODIMENT

Figure 1A:
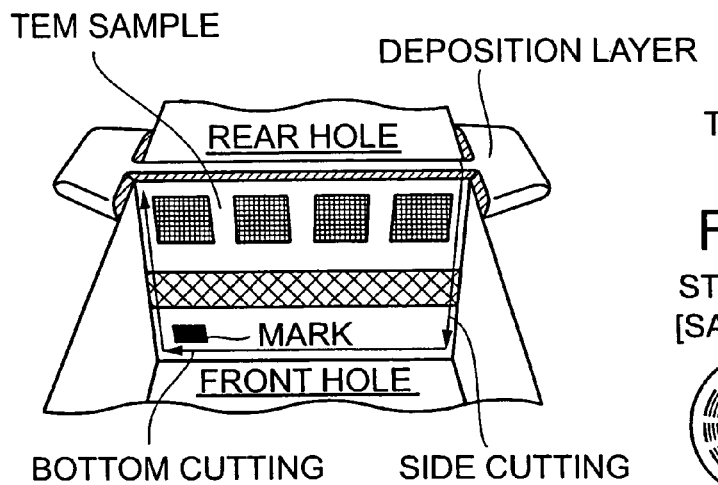
FIG. 1A is a view showing a TEM sample before being worked by the FIB device of the present invention so as to be cut out as a slice.
Figure 1B:
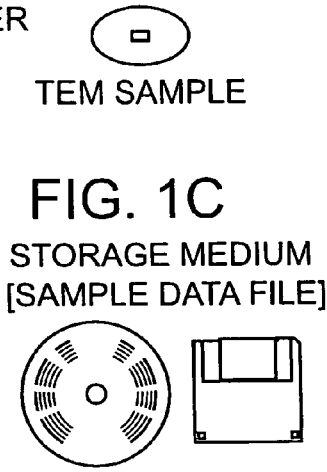
FIG. 1B is a TEM sample fixed on a mesh.
Figure 1C:
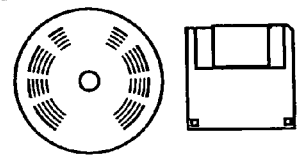
FIG. 1C is a recording medium constituting associated matter for the TEM sample.

The present invention simplifies and enables straightforward execution of management of handling of TEM samples that are troublesome due to their minute size, and writes sample adjustment information using markings to the TEM sample itself. Means for inputting information specifying the sample and information associated with the sample, means for converting the information into an encoded marking, and means for making a signal for controlling an irradiation position of an FIB in order to process the mark at the sample surface and apply the signal to deflecting means are provided at the focused ion beam device making the TEM sample. Information specifying the TEM sample or related information associated with the sample is then written in a step of thin-processing the TEM sample body. The writing position is taken to be a position at the periphery of the sample so as not to be an observation target for the sample as shown in FIG. 1A, with it being beneficial to decide upon the writing position at a prescribed position for classifying the sample. FIG. 1A is a view showing a TEM sample before being worked and cut out as a slice by the FIB device. The four mesh rectangles and the cross-lined horizontal stripe of FIG. 1A show some elements of the semiconductor device such as transistor, diode, conductive or insulative layer, so on. FIG. 1B is a TEM sample fixed on a mesh, and FIG. 1C is recording media such as a minidisk or floppy disk constituting associated matter for the TEM sample.

Figure 2:
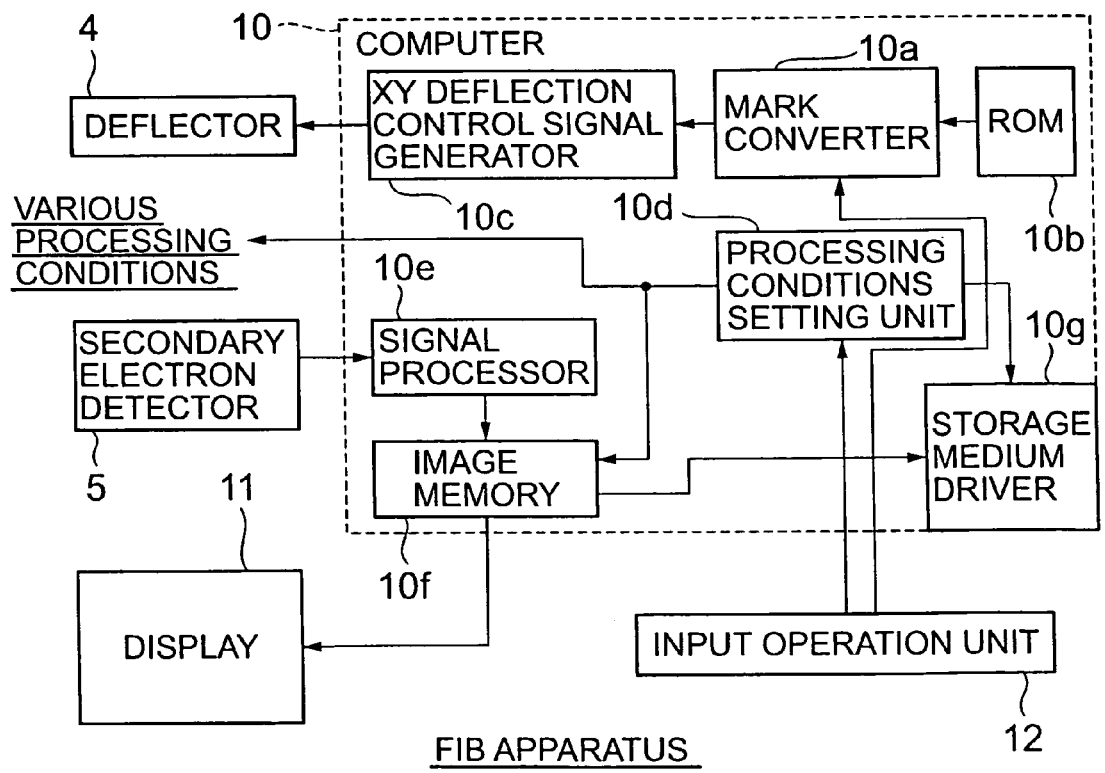
FIG. 2 is a block view illustrating the main functions of the FIB device for TEM sample processing of the present invention.
Figure 5A:
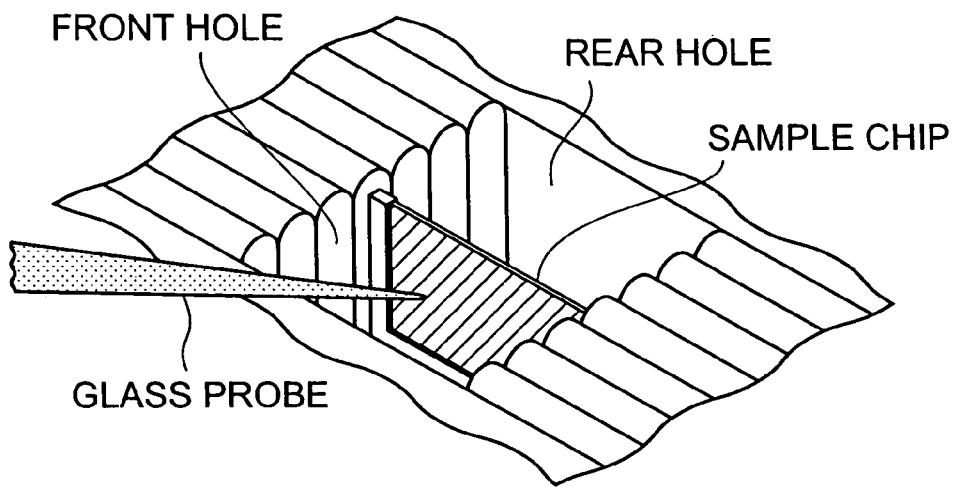
FIGS. 5A–5D are views illustrating processing for fixing a thin-processed slice of TEM sample onto a mesh.
Figure 5B:
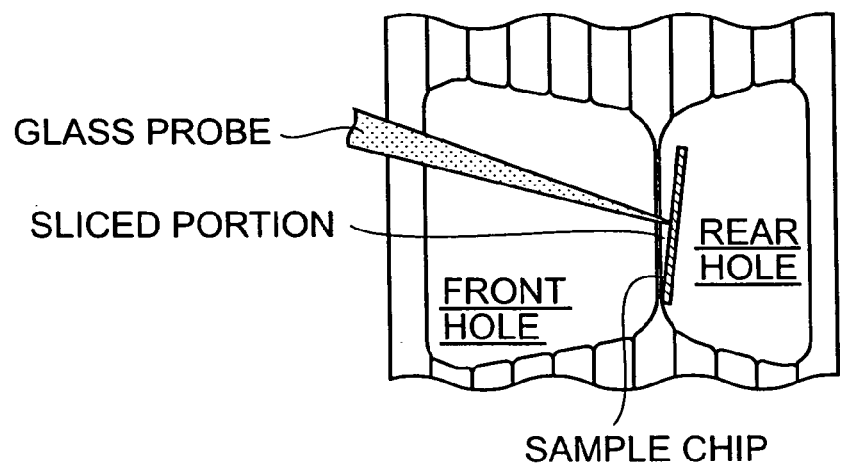
Figure 5C:
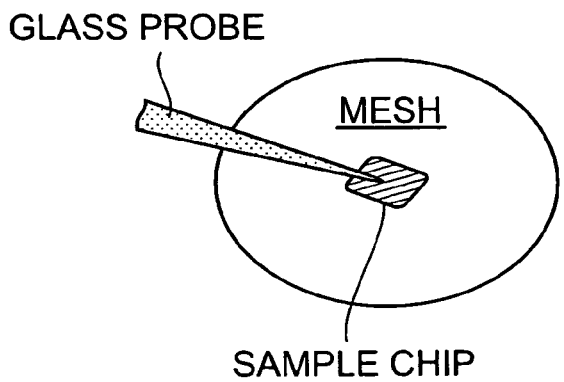
Figure 5D:
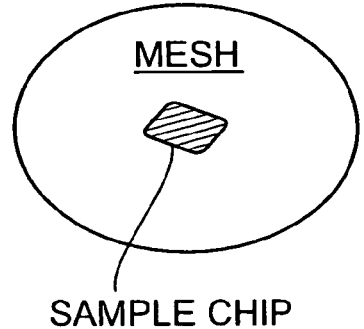
Figure 6:
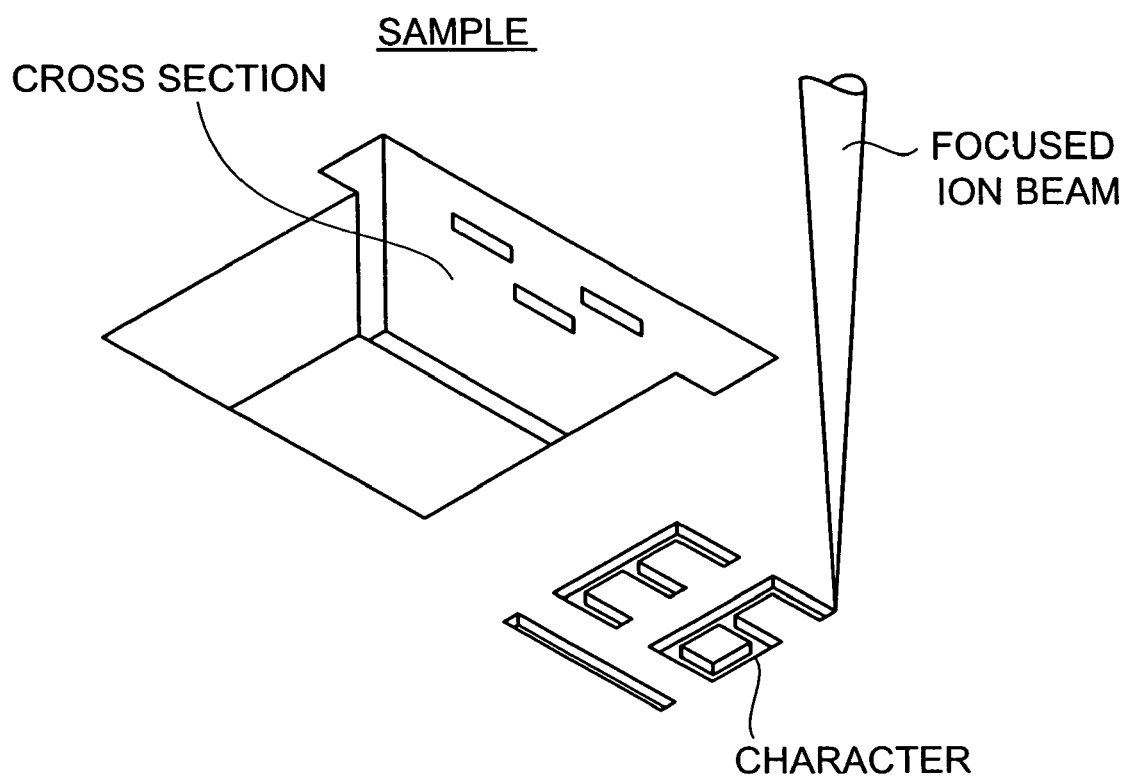
FIG. 6 is a view showing related technology for easily specifying an SEM sample and a TEM sample using FIB processing.

In a method of writing directly to a sample, the mark may be formed by etching processing using an FIB, by deposition by FIB irradiation while blowing a source gas, or by deposition using electron beam irradiation while blowing a source gas. The mark can be expressed in an appropriate manner using a number, bar code, or special character etc. The mark specifying shown in FIG. 2 is such that a ROM storing encoding rules is provided and information inputted using input means (input operation unit 12) such as a keyboard etc. is converted to marks in accordance with encoding rules stored in the ROM 10b. A computer 10 equipped with an FIB device for making the TEM sample identifies the mark. An XY deflection control signal for deflection scanning a charged particle beam so as to perform processing to write the mark onto the surface of the sample is then generated by an XY deflection control signal generator 10c and is sent to the deflector 4 of the device. The charged particle beam used in this deposition is not limited to an FIB. A device provided with an electron lens barrel for observation with processing then being carried out using an electron beam is also possible. It is preferable to keep irradiation with an ion beam to an absolute minimum due to the danger of the surface of the TEM sample incurring damage due to the ion beam and it is therefore preferable for the mark shape to be made by deposition employing an electron beam.

The TEM sample processing focused ion beam device of the present invention does not just have a function for simply making TEM samples, but also has a function for filing sample information for the sample being processed and information relating to the sample such as setting conditions for the sample at the time of processing and sets of observation images for during processing on a storage medium taking the specific information as an index. For example, processing conditions such as sample type such as 128 MDRAM, etc., observation part such as memory cell capacitor slice, beam voltage, current, and scanning speed are displayed, for example, in a table on a display 11. These conditions are sequentially written into a processing conditions setting unit 10d by the input means 12 via an image memory 10f, and stored on a storage medium as necessary taking the specific-information as an index.

One characteristic of the present invention is that although the TEM sample produced is observed using a TEM device, the sample produced is not just circulated by itself through a TEM, but is rather handled as a set with the storage medium storing the related information for the sample Further, the TEM device of the present invention is provided with a function for reading the mark encoded with the sample-specifying information and recognizing the specific information and a function for reading information relating to the sample taking the specific information as a key from the storage medium and displaying this on the display during observation of the sample. Namely, the TEM sample is set up at a sample table and the storage medium is set up at a driver of an associated computer functioning as a controller for the TEM device. The TEM device is provided with the configuration shown in FIG. 3. First, a mark for specific information written at a specific location at the lower left of a peripheral edge part of the sample put in the form of an image for a broad region of the TEM sample at a low magnification rate is put in the field of view. The magnification rate is then switched over to being a high magnification rate, and the pattern of the mark is identified. This is the same as normal image observation, with a signal detected using a secondary electron detector 15 being displayed at a display 21 via the image memory 20f after being processed at a signal processor 20e. A code-deciphering dictionary for identifying code of a mark is provided at a storage unit of a ROM 20b at the computer 20 associated with the TEM etc. Encoded specific information is then deciphered by a mark identifying unit 20a from the mark that has been pattern-identified by the signal processor 20e. Files are then specified taking the deciphered specific information as a key and the information relating to the sample is read from the storage medium installed at a storage medium driver 20g and taken into a work area. This related information is then displayed at the display 21 in the form of a table via the image memory 20f. This display image displays the TEM observation image in a window-divided manner, with switching over of the display also being possible. The operator can then confirm the sample-related information and observes the TEM sample. The related information is by no means limited to a table of information for working conditions, etc., and is also extremely useful in the operation of analyzing samples as a result of enabling comparison with images observed in working processes for the sample.

When observations are made with the TEM device, the observed images at this time and information relating to observed images for setting conditions for during this time, etc. is added to the files and accumulated. Namely, when observation conditions are inputted from the input operation unit 22, this condition information is transmitted to and set at the TEM body and is also sent to the storage medium driver 20g and stored in the storage medium as sample-related information for the sample. Next, when observation of the TEM sample is executed under these observation conditions, a signal detected by the secondary electron detector 15 is processed by the signal processor 20e and displayed as an observation image at the display 21 via the image memory 20f. This image information is transmitted to the driver 20g in order to be stored in the storage medium together with the observation conditions. Information relating to the sample is then sequentially accumulated in the file constituting the associated matter for the sample so that when this sample is observed by another TEM device, related samples can be shared by installing the storage medium in the driver. Further, information for the file accumulated in the storage medium constituting the associated matter can also be sequentially accumulated in the storage unit within the TEM device taking the specific information as an index. It is then possible to construct a database for TEM samples as a result of this accumulated storage. In the stage where the database is accumulated, it is possible to display and observe not just the TEM sample as specified by the specific information together with the related information on the display, but also, for example, to search, compare, and display another TEM sample constituted by a capacitor slice sample of a memory cell on the same DRAM. It is therefore possible to make comparisons with other samples worked under the same working conditions or to drive a search function of a computer taking one or more items of the inputted data as a key so as to enhance effectiveness of the observation operation.

Next, an example of information relating to the sample displaying the working conditions etc. in the form of a list etc. is shown.

1) Information relating to the sample itself
  a) Manufacturing process (MOS, memory, bipolar etc.)
  b) Process at the time of observation
  c) Manufacturing lot
  d) Observation position (coordinates on wafer, coordinates on chip)
2) Information relating to FIB working
  a) Working shape (width, depth, remaining width, etc.)
  b) Working conditions (acceleration voltage, beam current, etc.)
  c) Working information (name of person in charge, day and time of working)
3) Information relating to TEM observation
  a) TEM observation conditions (acceleration voltage, beam current, etc.)
  b) TEM observation information (name of person in charge, day and time of working)
  c) Presence or absence of processing prior to TEM observation (argon ion beam processing etc.)
4) Others
  a) Operator comments at each stage of operation In the above, the aforementioned related information is assumed but the present invention is by no means limited in this respect. Not just information for the time of observations by TEM but all information such as observation images occurring at the time of working processing and various values set at this time may be stored together in a single file taking specific information for all of the samples as an index. It is also possible to configure various databases by having the file usage conditions such as to enable searches not just taking this specific information as a search key, but also enable searches taking appropriate items as keys.

The present invention is by no means limited to the above example, and may include various modifications as described in the following.

For example, at the FIB device in FIG. 2, it is also possible to provide a "mark information/sample information storage unit" within the computer 10. Information M (information for mark shape etc.) for the mark written to the sample and information S (information such as sample name etc.) for the sample to which the mark is written may then be stored in a correlating manner at the "mark information/sample information storage unit". This mark information M may be provided from a mark converter 10a to the "mark information/sample information storage unit" and sample information inputted by the input operation unit 12 may be stored in the "mark information/sample information storage unit" as the sample information S.

In this modified example, after the sample with the mark written on is installed on the sample table of the TEM device, as with the example described above, a secondary electron image for the mark portion is acquired by the signal processor 20e. After this, the output signal of the signal process 20e, i.e., the mark information, is provided to a "sample information adder" provided within the computer 20 and read-in.

In this modified example, the computer 20 of the TEM device of FIG. 3 and the computer 10 of the FIB device of FIG. 2 are connected to each other by a network. The mark information M and sample information S stored in the "mark information/sample information storage unit" is then transmitted to the "sample information adder" on the TEM device side via the network and stored.

The "sample information adder" then compares the mark information from the signal processor 20e and the mark information M from the "mark information/sample information storage unit", and specifies a mark added to the sample currently installed at the sample table. The "sample information adder" specifies a sample name corresponding to the specified sample mark from the mark information M and the sample information S.

After this, as in the above example, sample observation is carried out by the TEM device. In this modified example, the computer 20 adds sample data for the sample specified by the "sample information adder" to electron microscope image data obtained by sample observation, with the electron microscope data being stored in a storage unit within the computer 20 as observation image data. Moreover, in this modified example, observation image information stored within the storage unit within the computer 20 is capable of being displayed on a CRT screen of the TEM device and the observation image data can be written to a floppy disc etc. at the storage medium drive 20g.

In the above, a description is given of a modified example of the present invention, but other modified examples may also be considered. With the TEM device of the above example, a secondary electron image of a mark is obtained for mark identification but it is also possible in place of this to obtain a transmission electron image for a mark written to a sample and read this mark information. In this case, a mark is caught in the field of view to carry out low-resolution observation, the resolution is then increased, and a transmission electron image of a high resolution may then be obtained for the mark.

Further, in the above example, a single sample is positioned on a mesh, but it is also possible to position a plurality of five or six samples on a single mesh and then carry out sample observation. In this case also, in the present invention, it is straightforward to obtain information relating to samples without making any mistakes from marks applied to the samples.

The TEM sample is written with a mark at a specific location of a peripheral part of the thin-processed TEM sample so as to be encoded with information specifying the sample and/or information associated with the sample. It is therefore possible to easily specify a particular sample within a large number of samples being managed. Further, as markings are provided at specific locations on the periphery of the TEM sample, it is possible to first capture the mark within the range of visibility at a low resolution and then easily execute accessing and observation of prescribed locations taking this mark as a reference point.

Further, with the TEM sample of the present invention, information relating to the TEM sample for the time of thin processing is filed taking sample-specifying information as an index in a storage medium constituting associated matter. It is therefore possible to collectively provide a large amount of information relating to the sample to an observer.

A focused ion beam device for TEM sample processing of the present invention is also comprised of a function for processing marks encoding sample-specifying information onto the surface of the sample and a function for filing inputted information relating to the sample in a storage medium taking the specific information as an index. It is therefore possible to file related information to the storage medium in a straightforward manner in the process for working of the TEM sample, so as to collectively provide the TEM sample and the storage medium constituting associated matter for the TEM sample.

Moreover, a transmission electron microscope of the present invention is also comprised of a function for reading the mark encoded with the sample-specifying information and recognizing the specific information and a function for reading information relating to the sample taking the specific information as a key from the storage medium and displaying this on the display. By then installing the storage medium of the associated matter in the driver together with the TEM sample to be observed, it is possible to carry out sample observation while displaying information relating to the sample such as that present in the processing conditions accumulated at the storage medium or the observation images occurring in the working processing at a display.

Further, if the transmission electron microscope device of the present invention is provided with a function for writing information relating to a TEM sample such as observation conditions at the time of observation etc. to an information file relating to the sample filed taking the sample-specifying information as an index, it is possible to further enhance the file accumulating the related information, and if the transmission electron microscope device is provided with the function for making a database together with other sample information, it is possible to configure a database so as to be enhanced every time observation of an abundance of samples is carried out.

What is claimed is:

1. A thin-processed TEM sample written with a mark at a specific location of a peripheral part of the thin-processed TEM sample encoded with information specifying the sample and information related to thin-processing of the TEM sample, the information related to thin-processing of the TEM sample being filed in a storage medium, which is installable in a transmission electron microscope, taking the sample-specifying information as an index.

2. A focused ion beam device for TEM sample working, comprising:

means for working marks encoded with information specifying a TEM sample onto the surface of the TEM sample; and means for filing information relating to the worked TEM sample in a storage medium installable in a transmission electron microscope taking the sample specifying information as an index.

3. A transmission electron microscope comprising:

means for reading a mark on a TEM sample from a secondary electron image of the mark encoded with sample-specifying information to recognize the specific information; and means for taking out information relating to the TEM sample from a storage medium using the sample-specifying information as an index and displaying the taken-out information on a display.

4. A transmission electron microscope according to claim 3; further comprising means for rewriting TEM sample relationship information based on an observation with an information file in the storage medium.

5. A transmission electron microscope according to claim 3; further comprising means for sequentially accumulating information files relating to the sample filed taking the sample-specifying information as an index and putting the information files into the form of a database.

6. A focused ion beam device for TEM sample processing, comprising:

means for writing a mark used to identify a sample onto a sample surface;

means for storing inputted information relating to the sample and information relating to the mark in a correlated manner; and means for transmitting information relating to the sample together with information relating to the mark to a transmission electron microscope connected to the focused ion beam device via a network.

7. A transmission electron microscope comprising:

storage means for storing information of a sample with a mark written into the sample together with information of the mark written into the sample;

a sample chamber for receiving the sample;

reading means for reading the mark written into the sample disposed in the sample chamber from a secondary electron image of the mark; and specifying means for specifying the sample disposed in the sample chamber based on information stored in the storage means and mark information obtained by the reading means.

8. A transmission electron microscope according to claim 7; wherein transmission electron microscope image data acquired for the sample disposed in the sample chamber is added with the information of the sample for the sample specified by the specifying means for storage in the storage means.

9. In combination: a set of one or more thin-processed TEM samples each written with a mark at a specific location on a peripheral part thereof, the mark being encoded with information specifying the sample and information relating to thin-processing of the TEM sample; and a storage medium having the information for each TEM sample filed therein using the sample-specifying information as an index.

* * * * *